United States Patent [19]

Kass

[11] 4,400,370
[45] Aug. 23, 1983

[54] METACHROMATIC DYE SORPTION MEANS FOR DIFFERENTIAL DETERMINATION OF LEUKOCYTES

[76] Inventor: Lawrence Kass, 1939 Ridge Rd., Hinckley, Ohio 44233

[21] Appl. No.: 242,662

[22] Filed: Mar. 11, 1981

Related U.S. Application Data

[63] Continuation-in-part of Ser. No. 129,680, Mar. 12, 1980.

[51] Int. Cl.³ .................... G01N 1/30; G01N 33/48; G01N 33/52
[52] U.S. Cl. .................................. 424/3; 8/644; 8/657; 436/63; 436/64; 424/7.1
[58] Field of Search ............... 424/3, 7, 7.1; 8/644, 8/657; 436/63, 64

[56] References Cited

U.S. PATENT DOCUMENTS

| | | |
|---|---|---|
| 2,126,852 | 8/1938 | Wolff . |
| 3,560,135 | 2/1971 | Yamayo ............... 8/657 |
| 3,617,185 | 11/1970 | Drantz ............... 8/657 |
| 3,985,500 | 10/1976 | Streck ............... 8/657 |

FOREIGN PATENT DOCUMENTS 4061 9/1979 European Pat. Off. .

OTHER PUBLICATIONS

Gurr, Synthetic Dyes in Biol., Med. & Chem., Aid Press, N.Y., 1971, pp. 54-55, 99, 117, 147-149, 395, 805.
Connis, Biological Stains, Williams & Wilkins, Balto, 9th Ed., 1977, pp. 43, 368, 404-407, 415-429.
Gray, Ency. of Microscop. & Michrotech, Van Nostrand-Reinhold Co., N.Y., 1973, pp. 398-399, 469, 561, 563.
Humdson, Animal Tissue & Tech., W. H. Freeman & Co., San Francisco, 1972, pp. 128-132.
Ruddell, Chem. Abs., vol. 89, 1978, Abst. #89: 54252q; Chem. Sub. Index, p. 2791cs.
Simpson, Stain Tech., vol. 45, No. 5, 1970, pp. 221-223.
MacConaill, Ireland J. Med. Sci., Jun. '64, pp. 243-250.
Sabin Bull., Johns Hopkins U., vol. XXXIV, #391, Sep. 1923, pp. 277-288.
Spiridonovitch, The Anatomical Record, vol. 27, Jan.-May 1924, pp. 367-373.
Moore, PSEMB, vol. 82, 1953, 601-603.
Hallberg, AEPA Med. Scand. Suppl., vol. 180, 1946, pp. 7-15.
Pilot, Use of Base Fluids for Counting Eosinophils, U. of Ill., May 23, 1950, pp. 870-871.

Primary Examiner—Anna P. Fagelson
Attorney, Agent, or Firm—Fay & Sharpe

[57] ABSTRACT

In the diagnosis and prognosis of various diseases as well as medical researches in relation thereto studies leading to differentiation, identification, enumeration and following the variations in human blood, leukocytes play a vital role. Heretofore, accurate detailed lengthy and arduous procedures were essential to such ends, if available. In a parent case, of which this is a continuation-in-part, it was found selective use of certain basic quaternary, metachromatic dye staining by supravital techniques made possible instantaneous optical differentiation of the five major individual leukocyte species. Here further research has revealed that with but one of the species of the dye class above one can by the same techniques make the foregoing determinations with regard to specific leukocytes including promyelocytes, myelocytes, metamyelocytes, band cells, T-cells and B-cells as well as the neutrophils, eosinophils, basophils and monocytes of the parent disclosure.

12 Claims, 3 Drawing Figures

METACHROMATIC DYE SORPTION MEANS FOR DIFFERENTIAL DETERMINATION OF LEUKOCYTES

CROSS REFERENCE TO RELATED APPLICATION

This application is a continuation-in-part of my copending application U.S. Ser. No. 129,680, filed Mar. 12, 1980, herein called the "parent application".

BACKGROUND OF THE INVENTION

1. Field of the Invention:

The present invention relates to an improvement in the field of cytology and more particularly a microscopic method of supravital blood analysis by which under normal white light illumination of a microscopic field optical differentiation, identification, comparisons and enumeration of each one of a series of leukocytes found in normal and pathologic human blood is made possible by use of a single pure dye without fixation and more accurately and rapidly than heretofore by either manual or automated differential leukocyte counters.

2. Description of the Prior Art

Ehrlich made biological elements more readily and easily recognized under microscopic examination and for photographic observation by use of dye stains (aniline dyes) to identify certain white blood cells. Ehrlich was the first to note that some dyes were metachromatic, observing that the staining of the cell or components such as granules of leukocytes causes the cell to take on a color different than that of the stain in solution or expected color from the stain. Basophils, for example, were observed to take on a color different from the stain. Other histological specimens other than blood cells have also been reported to stain in a plurality of identifiably different colors.

A review of the state of the art indicates it is almost universal practice, before staining (which presently uses a plurality of chemical differing dyestuffs in admixture) to employ a fixative procedure which may require up to an half hour treatment before the biological specimen is subjected to dye stain. Fixatives are generally preservatives and denaturants that often interfere with the sensitivity of the dye sorption. Illustratively, fixatives include formaldehyde both as liquid and vapor, absolute alcohols (methyl), picroformal, etc. Very often living cells do not stain using vital dyes and fixatives have been essential to staining the specimens. Cytochemistry includes considerable information on techniques developed to assure reproducible staining of blood cells. Many essential additives are normally unstable and deteriorate rapidly, thus making cellular identification difficult and in some instances unreliable. Dr. Thomas E. Necheles has observed in relation to leukocyte analysis that this "system has undergone little or no change in fifty years."

Dye staining does serve, however, as a means of discernment of otherwise undiscernable detail of conferring a color reaction on cells and their stainable components; metabolic, functional or pathological.

United States hospitals began leukocyte counting in the early 1900's, using the count as indicia as to whether emergency surgery was necessary, for example. In the U.S. alone, more than half a million differential counts are performed every day, most of them by manual methods. It is important that total white cell counts and differential cell counts be performed and reported without delay. Time is of essence and providing required analysis more rapidly is a desideratum.

The value of leukocyte counting having been established, the demand for rapid blood analysis has developed so that beginning about 1950 with the work of Mellors and Papincolaou (1952) development of automated differential leukocyte counting instrumentation means had developed into a plurality of instruments by 1980. The CYDAK unit was early used to investigate the feasability of blood cell classification which pointed up the importance of specialized staining procedures and features were extracted from optical density histograms of each cell image. The procedure established that cells could be differentiated into four of the five classes of leukocytes, namely; neutrophils, eosinophils, lymphocytes and monocytes. Young (1969) published results on an automated classification of five cell classes and Bacus in 1971 extended the differentiation.

However, it is understood that automated differential systems presently rely upon multiple dye usage and dye degradation systems or indirect fluorescent mesaurement using fluorescent dyes.

In the prior art staining of blood it has been observed that it is practice to use two or more stains in combination (Romanowski, Giemsa and Wright stains). These methods are difficult in practice to provide quality control. The methods require standardization in preparation of each dye stain component as well as in the method of specimen staining. In development of successful automated leukocyte counters, reproducibility of staining is even more important to verifiable analysis.

LARC stainer (used in commercial automated differential leukocyte counter) is reported (Mogler 1973) to be a mixture of some ten thiazine dyes, eosin Y and $2^1$, $4^1$, $5^1$ tribromofluorescein (P. N. Marshall). Present art stains most often are in fixative alcoholic solutions and employ two or more stains in combination. Accurate analysis of vital blood staining is made most difficult. With the difficulty presented in the controlled oxidation of methylene blue essential to Romanowski stains, for example, the problems of quality control of the added ten individually different dye stains as are used in combination become awesome.

It has been recognized in the art that the widespread standardization and adoption of a limited number of stains would ensure greater accuracy and reproducibility in cytological studies. Serious introduction of artifacts have been observed by use of fixatives and cause difficulty in interpretation and misinterpretation in leukocyte differentiation and enumeration. pH adjustments, heavy metal cations have been reported to prevent cytochemical tests from working in the expected manner. Some dyes, particularly azo dyes, are noted to demonstrate non-specific precipitation around cells; other degenerative changes in fixed blood samples include vacuoles, clover-leafing of nuclei, distortion cell shapes and smudges and interference with ideal staining. The importance of performing differential counts on as near living cells in the shortest possible time in order to obtain optimally useful and valuable blood cell analyses has been recognized. Alcoholic dye solutions interfere with supravital staining. So far as is known, freshly prepared water soluble stains exhibit a minimum denaturant effect upon supravital blood during examination. All dyestuffs are more or less toxic to the blood cells, but some are more so than others. It is material that the cells under examination remain living as long as possible. Rapidity of staining obviously shortens the exposure time, thus allowing greater opportunity to examine leukocyte cells before all vitality is lost. Automated differential leukocyte counting in less minutes is sought for.

Studies and review of the prior art of performing microscopic blood analyses and disease diagnosis has indicated it is not unusual for pathologists to warm the dye and the blood specimen to body temperatures (about 37° C.) before contact. Dr. Sabin had a "warm box" to insure temperature control.

It has also been noted that some dyes used in the prior art are quite temperature sensitive. The literature reports that cresylecht violet is not an operative stain above 30° C. It is considered important for the purpose of this method as disclosed herein that the dyestuff be useful to stain leukocytes at temperatures as high as 37° C. and no difficulty has been observed with the select dyes to temperatures of about 40° C.

In the parent application a relatively small number of metachromatic dyestuffs are disclosed as useful in identification of one or more species of leukocyte. Identification and differentiation was specifically related to polymophonuclear leukocytes (neutrophils), basophils, lymphocytes generally, and monocytes. A uniting commonality observed was that all of the dyes found to be operative for the purposes of the parent application metachromatically stained monocytes differentially from others in the above group.

The unusual qualities of the dye basic orange 21 (CI #48035) were observed in relation to the eosinophils, basophils, and monocytes, but as the B-cells are few in number they were intially overlooked. It was initially observed in the parent case that optical differentiation between mature and immature neutrophils appeared potential in that the mature granules were different in chroma from the immature granules which were more red and orange in comparison. As this group, including myeloblasts, promyelocytes, myelocytes, metamylocytes and bands are not always present in all blood specimens or present in significant numbers as is often the case with T-lymphocytes (or T-cells) and B-lymphocytes (or B-cells) they were not then all specifically identified as being metachromatically and differentially stained by basic orange 21.

Subsequent to completion of the work supportive of the parent application, continuing research on the use of this unique dye in similar blood donor studies established that it was reproducibly possible, using this selected basic cationic dye of the methine, polymethine and quinoline class to distinguish through metachromatic response certain lymphocytes. It is also possible further to identify at least ten recognized granulocytes and lymphocytic cells established in the art to be of vital interest to the health sciences.

Further, this differentiation was immediate, it required no complex biochemistry or arduous pre-treatment of the blood specimens. Additionally it was noted the dye exhibited minimum toxicity.

Micro spectrophotometric measurements were made with an aperture small enough to measure the color in the granules of supravitally stained leukocyte granulocytic cells. No other part of the cell entered into the measurements to any extent were found to provide extinction coefficients of the colors of the different leukocyte species which were consistently different and were often of an order of differences in hue, value or chroma of the order of 50 nanometers. These were recognizable peaks, consistent over many cells. It is understood that differences of the order of 5 nm are significant in microspectrophotometric measurements if the differences are consistent and reproducible.

Among the immature granulocytic cells immediately identifiable and distinguishable one from the other are myeloblasts and cells of the myeloid series, namely; promyelocytes, myelocytes and metamyelocytes. These are believed to be and are generally understood to be precursors of the polymorphonuclear leukocytes or neutrophils, which are also stained metachromatically so as to be readily and easily distinguished, identified and enumerated by the supravital blood analyses made possible by the advances disclosed herein.

As disclosed in the parent application, it is also practical at the same time to distinguish neutrophils, eosinophils, basophils, lymphocytes and monocytes from each other and from the foregoing precursors should they all be present in a specific blood sample under microspectrophotometric analyses.

Additionally, it has also been found that this unique dye provides an optically different pattern of color as well as a different density of each color of granule in band-lymphocytes. Thus, this quality of leukocyte cell can also be uniquely separated by optical differentiation from the other immature cells identified above. The differentiations in color, color arrangement and color density are also of such a degree of magnitude of difference that human counting of all the above individually named cells can be done by a competent operator. Evidence available also indicates automatic differential counting equipment will develop based upon and to be accommated by differences due to the presence or absence of color and the physical patterns established in the nucleus and by the relative number, size, arrangement or pattern and hue, value and chroma (color) and color density due to the number of granules in the cytoplasm.

Almost unbelieveably, but also demonstrated in the basic research thus far completed, is the further ability to differentiate B-lymphocytes or B-cells from T-lymphocytes or T-cells. Again, it is possible to specularly identify each of these important lymphocytes, one from the other, qualitatively and quantitatively using the same dyestuff in the same supravital, fixative free analysis as well as to distinguish and enumerate the T-cells and B-cells from each of the foregoing individual immature and mature cells including bands.

As has been disclosed in the parent application, the monocytes also respond metachromatically and are likewise identifiable and countable as there provided without conflict with the foregoing microscopic analyses of the lymphocytes as described.

Mention should also be made that blood platelets, small distinct, dust-like particles that serve one function of control of bleeding can be identified and counted by their orange staining. Their number is also a valuable indicia of blood quality.

Further discovery of the capacity of basic orange 21 to differentiate additionally myeloblasts and blood cells of the myeloid series as well as bands and T-lymphocytes and B-lymphocytes extends the original potential field of usefulness of the dye unexpectedly beyond the capacity recognized in the parent application. Supravital blood specimen fractions of fluids associated with healthy tissue or tissue suspected of abnormality such as plasma, lymph, serum, etc., containing one or more of the above cells after metachromatic staining may be examined microscopically to differentiate each species of cell indicated above permitting enumeration and comparative study.

The present advance in the art, coupled with the parent disclosure establishes unparalleled advance in hematology, cytology and immunology and the ability to plan and conduct researches in an unlimited area of human health. Need for costly reactants, invaluable research time and more accurate data assembly have been thereby measurably advanced.

The art of diagnosis of disease has a new horizon beyond the present limits.

Up to the present writing nearly a thousand different known dyes, some of which are no longer manufactured and were available purely by reason of extensive searches have also been investigated in an attempt to find leads on useful dyes for the broad purpose of supravital blood specimen fraction analyses and study. Trails of innumerable classes of dyes both from chemical structure and chromophoric group classification have been frustrating as to theory, metachromasia being very rarely found, however not exclusively in any known classification. It has been noted, however, that the basic quaternary cationic chemical class has produced more interest than any other group presently known.

In the studies basic to this application, twenty (20) methine and polymethine dyes of basic red, basic orange and basic violet hues were tested for leukocyte identification purposes. In the first group of nine basic reds only four caused instant staining of the nucleus of monocytes, but little or no staining of other cell types. This series includes basic red 13 of the parent application and basic red 35, 36 and 49 since investigated. Of the six (6) basic violet methine and polymethine dyes in the tests, basic violets 7, 15, 16 (disclosed in the parent application), 39 and 40 also instantly and selectively stained monocytes.

Six basic orange polymethine dyes were also subjected to practical testing. Basic orange 21 was unique in this series, not only staining monocytes distinctively, but an unexpected number of other leukocytes ecah were instantly stained, each in a differential way.

Significantly, the 20 polymethine and methine dyes represent the current world inventory of all available as well as commercially obsolescent dyes of the methaine and polymethine classification found in my researches of the prior dye art. The parent application reports a study of eighteen carbocyanine dyes, only one of which displayed similar metachromatic staining of monocytes. Carbocyanines, quinoids and methine and polymethine dyes are often of very similar chemical structure.

Detailed and specific study of the structure of basic orange 21 (Color Index 48035) disclosed in U.S. Pat. No. 2,126,852 led to testing of basic orange 22 (Color Index #48040). A study of the two chemical structures (as reproduced below along with actual testing led to astonishing results. Basic orange 22, does not exhibit metachromasia to any practical level of usefulness for the purposes herein.

CI-48040 Basic Orange 22

CI-48035 Basic Orange 21

Study of these structures indicates the only differences to be observed are that the indolyl radical of each basic orange indicated as B and $B^1$ in the foregoing structures varies only by a change in the methyl group from a 2 position in basic orange 21 to a 1 position in basic orange 22 and being substituted on a carbon in basic orange 21 and on a N in basic orange 22. The open 2 position in basic orange 22 also has an additional phenyl group in place of the methyl group so re-positioned in the structure.

In over three years of research with wide varieties and chemical classes of dyes no basis for predictability of metachromasia has yet been observed. More frequent metachromasia has been found among the basic cationic quaternary dyestuffs and relatively more often among the methines and polymethines.

Prior art references indicate that it was not unusual in supravital analyses to employ three concentrations of dye in three preparations of slides in such analyses as are an essential check on results. With basic orange 21, the color differentials are so separated and the colors so exceptionally vivid that one can readily distinguish primary from secondary granules, instantly, with one dye and one slide.

SUMMARY OF THE INVENTION

The present invention advances the art of cytology by providing one single basic quaternary cationic organic dyestuff of the methine and polymethine series which is selectively metachromatically sorbed by one or more peripheral blood cell leukocytes which provides unusual improvement in identification and differentiation between immature and mature members of the various species of the myeloid series and the mature white blood cells. Heretofore, cytochemical means and complex stains had to be used for blood cell differentiation, often requiring an hour or more of tedious preparation to prepare and microscopically analyze by differentiation and enumeration of a single species of known leukocytes.

In practice of the present invention it now is practical to differentially stain and identify with one single pure dye (others may be permissibly combined for specific studies) in a simple aqueous contact with a peripheral venous blood sample or fraction thereof, including leukocyte enriched specimens thereof, each one of the following species or types of precursor cells, white blood cells, platelets, etc., may be accurately and readily identified. These species include myeloblasts, promyelocytes, myelocytes, metamyelocytes, bands, neutrophils, eosinophils, basophils, B-lymphocytes, T-lymphocytes and monocytes. Platelets can also be identified and counted, but show no metachromasia.

Each of the leukocyte species, by sorbing or failing to sorb the dyestuff in some instances, becomes differentiated by reflecting a characteristic image having spectrally identifiably different colors, sorbing other colors within the normal light spectrum including primarily the visible light range but not excluding the infra red or ultra violet ranges which may become important to automatic equipment not limited by the human eye response. There is no need to rely or depend upon fluorescent dye response, however.

Thus, each one of the individual species recited can be differentiated from its neighbors, each species can be counted, the total count of any species present determined, each species can be studied as to its morphology, and many determinations made of great value to the health sciences.

Fundamentally, each of the above named white blood cells or leukocytes differentially sorb light from the same pure metachromatic dyestuff, depending upon the quality of the dye, the species of leukocyte, and the dye reception by elements of the specific cells present in the specimen fraction analyzed.

In the absence of fixatives, the basic dye of this invention is sorbed metachromatically so that each one class, type or species of leukocyte, lymphocyte or granulocyte reflects a characteristic light spectra or color different from every other class, type or species of blast, myeloid cell, leukocyte or ganulocyte present in the sample. THe strikingly vivid metachromasia of the single orange dyestuff of this invention has been, so far as presently known, unique and remarkable. Each species of the series including myeloblasts, promyelocytes, myelocytes, metamyelocytes, bands, neutrophils, eosinophils, basophils, B-lymphocytes, T-lymphocytes and monocytes so sorbs the single metachromatic stain as to reflect a distinguishing light spectra or color in the visible light range. Combinations of the dye of this invention with others as suggested in the parent application may be useful in some leukocyte analyses as indicated therein.

The primary standard for identification of this singularly novel dye and the newly identified dyes of the parent application are their spectral curves.

DETAILED DESCRIPTION OF THE INVENTION

This invention which is a continuation-in-part of a parent application U.S. Ser. No. 129,680 filed Mar. 12, 1980, which was based upon the discovery of a group of unique metachromatic dyes which could be used singly, but oftentimes in combination, to identify and distinguish five species of white blood cells, namely; neutrophils, eosinophils, basophils, lymphocytes and monocytes, one from the other, when present in a human blood specimen.

This invention provides further development of the discovery of the capacity of the dye known as basic orange 21 (Color Index 48035) which used alone in an aqueous medium using supravital blood analysis technique on a fixative-free specimen or fraction to stain in an unusual and distinctive metachromatic manner the previously identified series of human blood cells and platelets.

This individual species identification each one from the other reflects a remarkable order to differential.

While the foregoing blood cells have been priorly distinguished and identified by complex means, the prior art does not remotely suggest identification and differentiation of each of the foregoing species one from the other with a single dyestuff to be possible.

Figure 2:
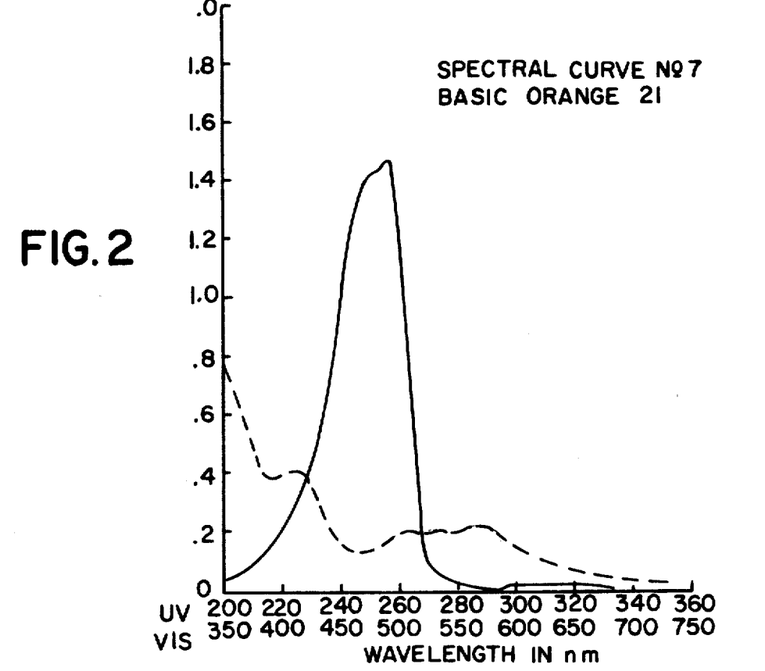
Figure 3:
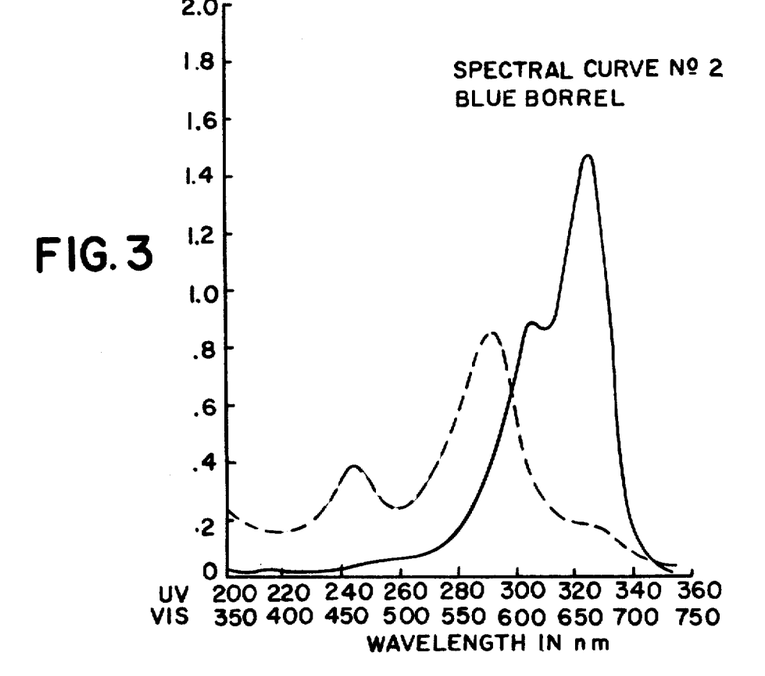

The patent identification is from the Color Index where basic orange 21 is also identified by the Color Index number 48035 and herein by the chemical structures and the spectral curves (FIG. 2). Spectral Curve #2 (blue borrel) (FIG. 3) is repeated herein as it is suggested in the parent application for use in combination with basic orange 21 for some purposes. Note the upper curve which in general has the lowest peaks and greater frequency of changes in slope, represents ultra-violet light response; while the initially lower curves, having in general fewer and higher peaks are visible light response curves.

While it is not intended to be bound by theory, it is well known that almost any foreign additive has a tendency to denature proteinaceous materials. Heretofore, use of fixatives in preparation of blood samples for staining has been universal practice. Experience has indicated that fixing interferes with the co-operation between the metachromaticity of the cell and the metachromatic quality of the dyes of this invention. Troublesome artifacts in the field are also avoided by the simple expedient of supravital, fixative free, specimen use using a supravital technique.

In the practice of this invention, staining is sufficiently instantaneous so that at normal blood temperatures (37° C.) the cytologist does not have to wait or resort to fine cytochemistry practices before cell dye development occurs and spectral differentiation between the previously enumerated family members of leukocyte, lymphocyte and granulocytic cells before beginning his microscopic studies, either manually or by automated differential leukocyte counting systems.

Types of fixative free blood samples that can be used:
1. Anticoagulated (E.D.T.A., citrated, heparin) whole blood.
2. Suspensions of leukocyte obtained by dextran and/or gravity sedimentation of anticoagulated whole blood.
3. Samples of whole blood treated with hypotonic solution lyse red blood cells, leaving primarily white blood cells and platelets behind.
4. Samples of other body fluids, like spinal fluid or pleural or ascitic fluid, as well as samples of joint fluid where white blood cells are of interest.

While the present invention does not specifically provide for an automatic differential leukocyte counting system, such systems have been under in-depth examination.

The College of American Pathologists Conference in Aspen, Colo., August 1975, has published a series of papers delivered at that time in a collection entitled "Differential Leukocyte Counting". These reports provide development and "State of the Art" interest in automatic differential blood cell counting computers. Attention is also directed to U.S. Pat. Nos. 3,916,205 and 4,146,604 (Kleinerman) where certain fluorescent dyes are used in particular combinations for automatic differentiation of certain leukocytes and other blood cells based on fluorescent light response. These references are deemed pertinent to the subject matter and ends of this disclosure. It is to be additionally noted that Kleinerman relies upon cell fixation, customary in microscopic studies of leukocytes.

The prior art indicates several levels of discrimination in the performance of leukocyte differential counting. Basic or primary is differentiation between polymorphonuclear cells and "mononuclear" cells. On an intermediate level, the differentiation of polymorphs into neutrophils, eosinphils and basophils and the separation of "mononuclear" between monocytes and lymphocytes is said to be possible in principle.

An apparent third level of difficulty involving differentiation of neutrophils into immature and mature forms and the division of lymphocytes into normal and reactive types was originally recognized and mentioned in my parent application. So far as is presently known this disclosure provides the only method of simply differentiating by means of one single pure dyestuff the blasts, myeloid series, bands, polymorphonuclear leukocytes (neutrophils), eosinophils, basophils, B-cells and T-cells as well as monocytes and platelets with a single dye and single specimen fraction.

The present state of the art in automated differential leukocyte counters is in the development stage insofar as the use of white light and a simple aqueous dye is concerned. Manual differentials with preliminary complexity appear to be principally relied upon. Automated differential counters are said to be of two general classes or groups: 1. pattern recognition systems and 2. cytochemical differentiation systems. It is understood that staining methods of the prior art have been used with greater or less success and machine operators can monitor the operation on a cell-by-cell basis. Usually only 100 cell differential counts are made. Cytochemical systems, while precise, have yet to develop satisfactory calibrators and require highly qualified operators.

In a brief survey of the fluorescent methods of the prior art, the following points are of record. 1. At least two light sources are essential including violet and ultraviolet light; 2. A third light source appears needed as well. 3. The system is understood to require a plurality of fluorescent dye stains to identify and differentiate the species of leukocyte. 4. The system requires alcohol-fixed blood smears. 5. Required staining time is of the order of ten minutes and rinsing for one minute followed by drying. 6. There appears to be a decreasing order of fluorescence intensity from (a) eosinophils to (b) neutrophils to (c) monocytes to (d) lymphocytes. (Basophils identification is not reported). 7. In a flow tube system, the blood cells are fixed with formaldehyde and stained with three different stains. 8. Detected leukocyte fluorescences are differentially counted and classified by means of ratios of fluorescent light. 9. One patentee discloses identification of only four of the five leukocyte species. 10. Three fluorescent dyestuffs are specified which must be combined to produce a "single dye" composition which combination of dyes appears essential to the operation or method, not merely advantageous.

In the present disclosure, only ordinary white light is essential. No variation in its intensity is required. It is feasible in use only one of the disclosed dyestuffs or dye stains of the parent application to employ truly a "single" pure dye. However, it has also been discovered that the pure dyestuffs of the parent application as is true here can also be further used both combined and alone to enhance or augment spectral differentiation in a single human blood specimen analysis.

The methods disclosed are based on a supravital technique. There is possible a continuous monitoring system in hospital diagnosis and treatment where continuous critical white blood cell observation directly on the patient would be a desired end such is within the potential here.

The term supravital stain and supravital staining does not preclude the possibility of continuous perfusion through a shunt circuit from the blood vessels of living organisms and continuous monitoring of all possible white blood cells as they are passed through a specialized by-pass tube for observation and count.

It is kmown that most dyes are toxic when used under supravital conditions. Basic orange 21 is the least toxic dyestuff noted to date for the purposes herein. It has been noted in the prior art that white cells are easily damaged if all red cells are stained in a warm box at 37° C. Prior art has also noted that if a group of cells are stimulated or damaged, reaction to dyes may be markedly changed. It is not unusual that some prior art dye staining requires relatively long periods, on the order of an half hour to obtain maximum dye intensity. The lymphocyte and leukocyte dye of this invention stain almost instantaneously, no time is required after contact. Thus the cells are subjected to examination in the least denatured form presently known. Excessive times of exposure may interfere with the sharp initial differentiation.

Based on limitations inherent in panoptically stained specimens, over the past several decades a number of cytochemical tests have been devised to more precisely distinguish one type of blood cell from another. In general these tests are designed to detect increased amount of one type of substance in a particular cell compared to another, or to detect a substance(s) within a characteristic cellular organelle in one cell compared to another. For example, activity of nonspecific esterase is unusually high in monocytes and this activity appears to be particularly sensitive to inhibition by sodium fluoride. Likewise, identification of granulocytic cells depend for the most part upon demonstration of properties of lysosomes. For these purposes, detection of myeloperoxidase and specific esterase activities have been useful as cytochemical tests. Lysosomal granules of eosinophils contain myeloperoxidase that is resistant to inhibition by sodium cyanide, and granules of basophils stain metachromatically with a variety of dyes, due in part to their high content of cationic substances like heparin.

Extension of studies with basic orange 21 have shown a surprising development over the parent application hereof. It was initially noted that basic orange 21 had some unusual qualities and this continuation-in-part verifies the initial observations therein noted.

As will be noted herein, monocytes show a non-staining nuclear reaction but are identified by cytoplasmic and granular color differentiation.

Compared to conventional cytochemical stains for identification of monocytes, neutrophil leukocytes, eosinophils, and basophils, supravital staining of peripheral blood leukocytes by basic orange 21 has several advantages. It is advantageous because it is rapid, requiring less than two minutes for maximal color development. It is also advantageous because it avoids the use of synthetic substrates and complex azo dyes and couplers as used in conventional cytochemical tests. Prior art cytochemical tests are difficult to interpret because of nonspecific precipitation of color reagents, deterioration of substrates and the need for complex adjustments of pH and metallic ion content.

The supravital stain technique utilizing living blood cells and their differential affinities for supravital staining of these cells with dilute aqueous fixative free dyes avoid artifacts that often occur with conventional fixatives. We submit that the vital staining technique provided herein defines a more accurate reflection of cellular locallization of the dye (e.g. lysosomes, fibrillar structures, nuclear chromatin) than presently used conventional stains. With continued experience and improvements in the automated technology of differential blood cell counting, supravital fixative-free staining of peripheral blood leukocytes introduces an important addition to field of cytochemistry.

It should be noted that the nomenclature identifying basic orange 21 is from the Color Index. It is also identified by other names as well. Because of possible confusion of nomenclature and the fact that while basic orange 21 is uniquely operative, its next neighbor in the Color Index, basic orange 22, of almost identical chemical structure (supra) is inoperative and shows no metachromasia for present purposes, we rely upon the spectral curves and the known chemical structure to identify the specific quaternary cationic dyes of this invention. It is interesting to note that all the operative dyestuffs of this invention metachromatically identify monocytes.

Figure 1:
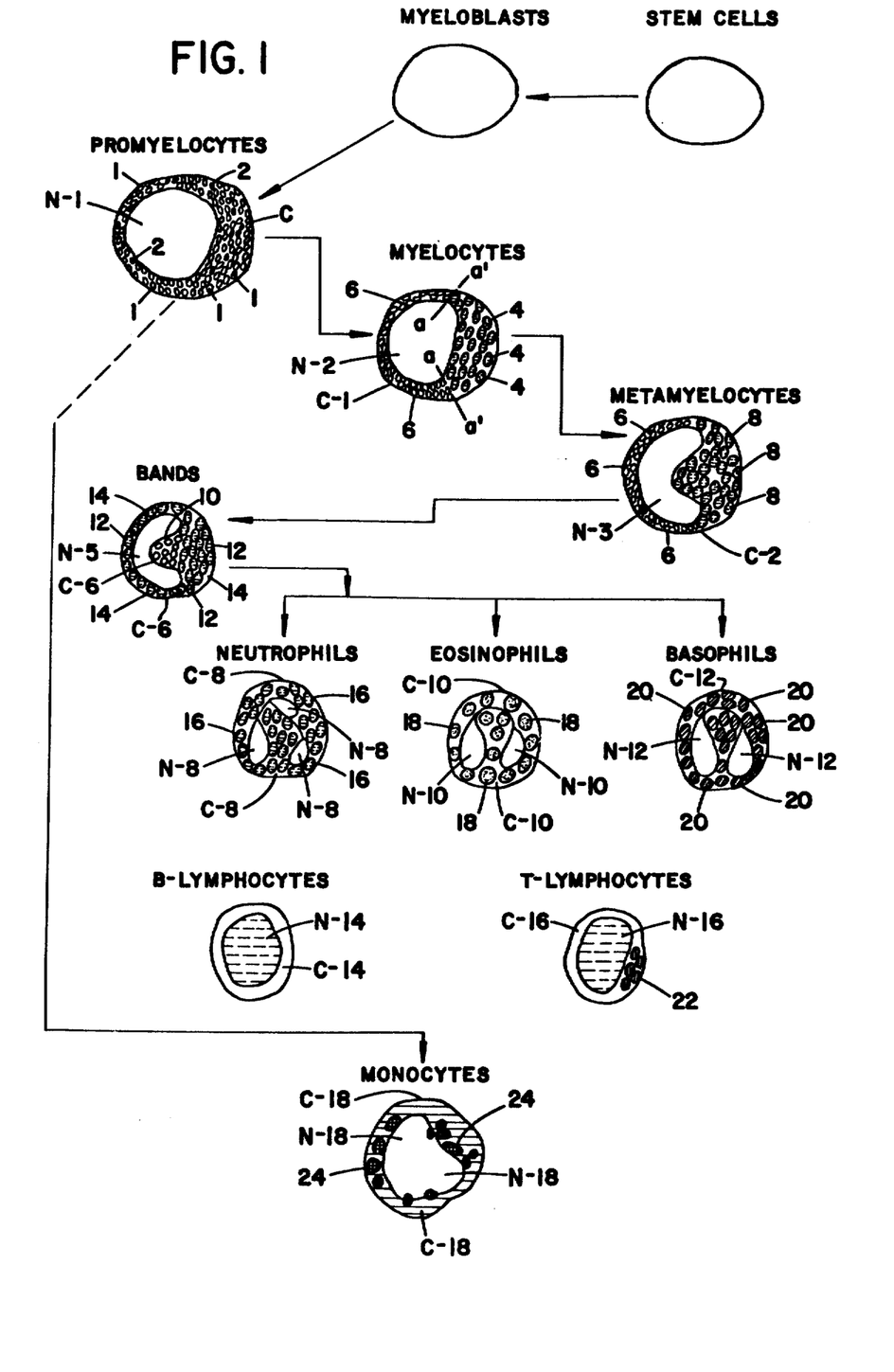

It is convenient at this point to refer to FIG. I as an aid in understanding leukocyte identification and differentiation as provided by the advance in the art herein.

Limitation to black and white illustration of FIG. I and the fact that the essential representations involve three dimensional objects and color variations which are not accurately identified by the grossness of language is an unfortunate loss of letters patent issue in black and white.

All blood cells appear to originate from undifferentiated stem cells called mesenchymal cells. Immediate descendants of the stem cells are called blasts, and the specific myeloblasts are understood to be progenitors of the leukocytes differentiated and made identifiable and enumeratable by their supravital analyses when exposed to basic orange 21 in a fixative free aqueous environment. Myeloblasts are identified herein by the absence of granules of lysosomes which characteristically identify the three descendant cells of the myeloid series by their metachromatic color sorbtion. The three descendant cells, namely; promyelocytes, myelocytes and metamyelocytes are each separately identified by the metachromatic and differential color and color distribution as will be described.

Promyelocytes are readily identified by the following manual or automatic observations. They are generally largest in size of the myeloid series shown. The oval nucleus N-1 is not stained by basic orange 21 and is relatively a large part of the total granulocytic cell. The cytoplasm C thereof is closely packed with large numbers of relatively small primary granules of an orange-red color 1, and a few scattered violet granules 2 may also be observed generally distributed amongst the mass of orange-red granules.

Myelocytes also possess a non-stained ovate nucleus N-2 of slightly reduced area (volume). The outstanding distinguishing fact is the definite development in the myelocyte of larger secondary yellow granules 4 in a generally thickening crescent of the immature myelocyte cell. Dual imaginary lines $a-a^1$ bracket and delineate the increasing number of larger secondary yellow granules 4 of the myelocytes from the decreasing number of smaller orange-red primary granules 6. One can observe that myelocytes are distinguished from promyelocytes by the noticeable isolated component of developing secondary larger yellow granules 4.

Metamyelocytes also have a non-stained nucleus N-3 which begins to exhibit developing lobular pattern as distinct from the priorly described ovate form of the first cell in the myeloid series. The diminishing mass of smaller, primary, orange-red granules 6 now becomes a minor proportionate area of the total area of the observed cytoplasm C-2 of the cell. Larger secondary yellow granules 8 appear to displace a significant central portion of the previously ovate unstained nucleus N-3, which defines the change intended by the verbal expression—from ovate to lobular—.

Bands are progressively distinctive and have been set apart from the first three cells described showing metachromatic staining of the granules and which are members of the myeloid series.

So far as presently known, bands have not been heretofore distinguished from all other leukocytes by the metachromasia of any dye.

Bands are distinguished from all other leukocytes by an unstained lobular formed nucleus N-5 which, along with the overall band size has noticeably decreased in area (volume) as compared with the prior leukocyte cells of the myeloid series. Additionally the lobular form of the unstained nucleus N-5 has become more bifurcated by further inward growth of the cytoplasm C-6. Growth by number increase of secondary yellow granules 12 in the cytoplasm has displaced all but a very small cluster of remaining primary, smaller, orange-red granules 10. Note that the cluster of red granules 10 are specifically located in the inward protrusion or movement of the cytoplasm C-6 tending to segment the nucleus N-5. Larger, secondary yellow granules 12 have succeeded to take over the cytoplasm C-6 except for this characteristic contrasting color group of bands. The important point of separation of bands is the small cluster of red granules 10 in cytoplasm C-6 at 10.

This outstanding point of differentiation of bands from all other leukocytes is suggested as extremely useful in development of automated equipment adapted to perceive the small primary orange-red granules 10 surrounded by a large preponderance of secondary yellow larger granules 12.

Ability to easily, rapidly and certainly distinguish, identify and enumerate bands from all other leukocytes with but a single dyestuff as described above is beyond expectation and beyond any known theory of band function.

Neutrophils are mature white blood cells and were known to be recognizable from the five main classes of white blood cells of interest in the parent application. Further detail of interest has now been established.

Neutrophils, eosinophils and basophils, in the absence of color reproductions as in the drawings, are all of relatively similar physical configuration. Using basic orange 21 as the sole supravital dye in a fixative free environment, neutrophils are identified by secondary granules 16 in the cytoplasm C-8 which are mainly yellow. The nucleus N-8 is not stained and is generally segmented. The large secondary yellow granules 16 constitute the major area (mass) of the cytoplasm C-8.

Eosinophils also possess a segmented unstained nucleus N-10, but the large secondary granules 18 are differentiated from the neutrophils and basaophils by their orange color which is the characterizing and main feature of the cytoplasm C-10.

Basophils segmented nucleus N-12 is also unstained by basic orange 21, but the secondary granules 20 differ from the granules of the neutrophils 16 and the eosinophils 18 by metachromatically staining basophil granules 20 a bright crimson color having a faint blue tinge or undertone.

Note in the indicated cell lineage that each of the leukocytes shown in the figure, neutrophils, eosinophils and basophils actually are derived from their specific precursor bands. The figure as drawn does not indicate this progression in detail. Promyelocytes are indicated as precursors of monocytes.

B-lymphocytes and T-lymphocytes have essential oval nuclei N-14 and N-16, respectively. Each of which nucleus N-14 and N-16 stains a similar yellow. The cytoplasm C-14 and C-16 in each case remains unstained. Again, one characteristic of the cytoplasm C-16 of T-lymphocytes clearly differentiates T-lymphocytes from B-lymphocytes. This is the presence of the small cluster of red granules 22 in the cytoplasm C-16.

A rather remarkable observation, also noted in the parent application, has been the fact that the monocytes have been acted upon by all of the basic quaternary cationic dyes which have been metachromatically active for the purposes of leukocyte identifications and differentiations.

With basic orange 21, the monocytes do not stain as to their generally ovate nucleus N-18. However, the cytoplasm C-18 acquires a pink cast in which are discernable a scattered, relatively small number of crimson and pink granules 24 differing in hue, value and chroma sufficiently from the "pink" cast of the cytoplasmm C-18 to be clearly optically differentiated from cytoplasm C-18 which is of a generally similar pink coloration.

Identification and enumeration of monocytes has been simplified by discovery as also described in the parent application with the set of unusual dyes disclosed. The standard fluoride sensitive non-specific esterase reaction cytochemically used for monocyte identification often requires an hour or more to complete and requires accurate cytochemical manipulation to be successful. With any one of the disclosed dyes, the dyeing of buffy coat suspension, whole blood or separated fractions and examination can be performed simply, without chemical adjustments, in the order of minutes. Staining of monocytes by the present application method using only basic orange 21 is instantaneous as the cytoplasm, and the granules in the cytoplasm.

It should be noted that the metachromatic dyes may ultimately stain the cells to a point where identifications are lost. Thus, the color differences reported in this disclosure may be lost, or diminished to a great degree if analyses are not promptly performed. As practical staining occurs promptly, no extended waiting period for maximum differentials is, however, necessary.

In the prior art identification and differentiation of monocytes has been accomplished by time-consuming and complex cytochemical treatment of the cells involving non-esterase reaction, fixed cell preparation, hexazotization, pH adjustment and dye staining with multiple dyestuffs requiring about sixty minutes to accomplish what can be done with any one of the dyes of the parent application, if desired, in less than a minute by a simple dye and blood sample contact with an aqueous system. With the specific dye of the present process as herein disclosed, there is also instantaneous preferential staining of the cytoplasm of monocytes.

The unique dye is prepared for the proposed end use and for the purposes of this invention in filtered aqueous solution at approximately 1% concentration of the pure basic orange 21 in distilled water. The dye concentration is not particularly critical but permits variation. It is preferred that aqueous solutions be used while fresh and that toxic additives not be included. Interference with the metachromatic reaction between dyestuff and the spicific type or class or leukocyte may be totally inhibited by the presence of any of the known classical fixatives.

The definitive language "supravital" as used herein is an important limitation. It is applied to the original blood sample and is applied to living cells freshly removed from a living organism, or one freshly sacrificed, or equivalent. As the term is used here it is intended to exclude all "fixatives" but permits use of anti-coagulants (heparin, E.D.T.A., etc.). The blood cells may also be removed from bone marrow, urine and other biological specimens containing them, including as illustrative lymphatic tissue and spleen.

The general practice of this invention is illustrated by the following.

A 1% solution in distilled water is made up of the selected basic quaternary cationic dye, here basic orange 21. If practice indicates it necessary, one or more of the subject dyes can be blended together as solutions. Basic orange 21 (Spectral Curve #7) is specific.

The aqueous solution of the selected, previously identified, single pure dye (or one can employ combination of one or more of the pure dyes as are disclosed in Tables I and II, as illustrated in Table III of the parent application) is solubilized to produce a simple aqueous dye solution. (Consideration of various volumetric proportions of the aqueous dye solution, and various strengths of aqueous dye solutions may provide optimum conditions for various specific cytological analyses.) Some experimentation may lead to specific combinations having particular advantage and is contemplated by but beyond the scope of this disclosure.

Blood samples may be made available from various sources but fresh samples of venous blood from which erythrocytes have been removed (centerifugation, hypotonic lysis, gravity sedimentation, density gradient sedmentation, etc.) or the sample may be a plasma enriched with white blood cells by known physicochemical techniques. Fixatives are avoided.

It is preferred to combine the aqueous dye and blood sample, both as freshly prepared, at the temperature of normal blood or body (about 36°-40° C.) where the analyses planned so indicates. More rapid and sharper staining at the higher temperature is generally obtained. Basic orange 21 does not appear temperature sensitive or critical.

Dye and blood solutions work well when combined volumetrically at a ratio of about 1:4. Gently agitate the mixture for several seconds and examine a drop of the mixture immediately as a wet mount using a glass coverslip under a light microscope or automated differential luekocyte counting device, if available. Other means of contact between the dye and blood cell include using known media, illustratively gelatin, emulsions, etc., impregnated with the dye at about 1% dye concentration. Fixing the sample seriously interferes with the unusual metachromatic co-action of the dyestuffs of this invention with the leukocytes.

Using basic orange 21 die makes possible to identify and distinguish the following one from the other if they are present together: myeloblasts, promyelocytes, metamyelocytes, myelocytes, bands, neutrophils, eosinophils, basophils, B-lymphocytes, T-lymphocytes and monocytes. Outline of the means of differentiaton for enumeration and other study have been priorly developed in the Figure.

The examples included herein as illustrative will assist one skilled in the art to appreciate the potential of the novel method proposed. Not the least of the advantages of the method are leukocyte counts (total), leukocyte counts of species, diagnosis of diseases, particularly leukemias, and the monitoring of patients receiving a variety of critical treatments, illustratively, chemotherapy, radiation therapy, ACTH, etc.

It is known that identification and enumeration of all of the species of leukocytes is often critically important in diagnosis and treatment of disease.

The examples which follow the detailed description of the invention are intended to illustrate the utility of the invention and its practice. Obviously, they are not exhaustive nor are they to be considered limiting.

EXAMPLE I (Basic Orange #21 -- Spectral Curve #7)

An extensive series of methine, polymethine, quinoid and/or carbocyanine dyes were obtained based upon the initial discovery that basic orange #21 was found to be unusually methachromatic in relation to differential staining of white blood cells. Of the large group of dyes tested having not only the general structural similarity of the above class, but as in the case of basic orange #22, the structure varied by what was considered to be minor substituent differences (supra).

Only basic orange #21 of an expanded group over the parent application was found to exhibit the unusual methachromasia disclosed herein.

50 ml. of peripheral blood was obtained from normal individuals in a series of heparinized tubes.

Duplicate tubes were admixed with 10 ml. of a 1% solution of basic orange #21 dyestuff in distilled water at about 37° C. The temperature has not been observed to be critical with this dye use.

Under microscopic study eosinophils originally described as having brown granules were more accurately described here as having large orange granules in the cytoplasm with a non-stained lobular nucleus. Basophils were observed to have a similar geometric configuration, but the granules were bright crimson in mass tone with a faint blue tinge. The nucleus was also lobular, and not strained. Monocytes were clearly differentiated by non-stained oval nucleus and a pink cytoplasm containing crimson and pink granules. Non-stained may include very pale casts depending somewhat on the time before reading the slide.

Quite remarkably, the differential staining of both mature and immature neutrophils was more specific than any dyestuff heretofore observed in our studies or reported elsewhere in the prior art. Mature neutrophils were spectrally identifiable by the mainly yellow larger granules in the cytoplasm and the lobate unstained nucleus. Immature granules (see FIG. 1) were observed to be identified by orange-red granules in the cytoplasm and a generally oval, non-stained nucleus.

EXAMPLE 2

T-cell rich and B-cell suspensions of human blood were prepared from 50 ml. specimens of peripheral blood obtained from mormal individuals in heparinized Vacutainer tubes by passage of Ficoll-Hypaque enriched fractions through microcolumns of nylon mesh gauze. T-cell rich and B-cell rich suspensions were eluted from the columns using controlled temperature conditions with selected different buffers as is known in the prior art.

Fractions of these recovered suspensions were subjected to immunologic analyses using T-cell rosetting for T-cells and surface immuno-globulin detection for B-cells. One drop of a 1% aqueous solution of basic orange 21 dye was incorporated into 5 drops of the recovered suspension in separate test tubes. Each tube contained approximately $2 \times 10^6$ lymphocytes. Lymphocytes identified as T-cells by virtue of T-cell rosette formation were microscopically observed to contain small groups or clusters of 5 to 10 or more red granules. Lymphocytes identified as B-cells by immunological methods exhibited only a rare red stained granule in the cytoplasm; most of the B-lymphocytes had no red granules present in the cytoplasm. The nucleus was oval and stained yellow in both T-cells and B-cells. The dyes rhodanile blue and carbocyanine K-5 (parent case) also stained lymphocyes generally but the granules were not as vivid as with the basic orange 21 dye.

Use of basic orange 21 provides a new, rapid method for identifying, differentiating and counting T and B lymphocytes or cells over the present methodology. Present methods involve use of unstable biological reagents, (sheep cells), require radioisotopic techniques which are costly and time demanding, require control of many variables including temperature, pH of incubation media, etc., which no longer appear necessary.

EXAMPLE 3

Peripheral blood samples of normal healthy persons do not exhibit generally immature luekocytes of the myeloid series including promyelocytes, myelocytes and metamyelocytes. These are found in certain diseased states, illustratively. invasion of the bone marrow by cancer, a "leukemoid" reaction as found in serious infection, chronic granulocytic leukemia, etc. In a series of trials it was observed that basic orange 21 stains diseased leukocytes colors that are at a variance with normal leukocytes. Thus, by comparisons of standard or healthy normal periphery blood samples it was observed that the granules of eosinophils stain a dark orange, whereas granules of eosinophils of persons with an acute infection stain a golden yellow.

EXAMPLE 4

A 48 year old woman patient terminally ill with breast cancer developed septicemia and a high fever shortly before death. At that crucial time her white blood cell count rose to 45,000 per $mm^3$. By use of the standard Wright's stain, it was established that 60% of the peripheral blood leukocytes were bands having a characteristic unsegmented nucleus.

Specimens of the patient's blood was stained with a 1% aqueous solution of basic orange 21 as a supravital stain without fixatives.

Bands were identified by the consistent presence of a small cluster of red staining (primary) granules amidst a larger number of larger (secondary) granules which were metachromatically stained yellow as well as the typical unsegmented nucleus.

Thus it was possible to make positive identification, differentiation and enumeration of the band forms on the basis of their cytoplasmic maturation and color differentiated primary vs. secondary granulation rather than solely on the size and shape of the nucleus.

EXAMPLE 5

Five patients known to have untreated chronic lymphocytic leukemia were donors of peripheral venous blood specimens.

Using conventional immunologic markers (T-cell rosette, Ig G surface markers) these were established to be all B-cell in type.

Five drop specimen fractions of each donor sample were admixed with one drop of freshly prepared 1% aqueous, filtered, solution of basic orange 21 in the series of test tubes. Slides viewed as a wet mount with the light microscope showed none of the cells to contain a cluster of red granules in the cytoplasm as is characteristic of T-lymphocytes or T-cells. All the diseased cells stained yellow in the nucleus, as do normal B-lymphocytes or B-cells.

These test results, without long delay and tedious cytology, confirmed the first result of absence of T-cells and reinforced the present theory that chronic lymphocytic leukemia is a B-cell associated disease.

EXAMPLE 6

A 62 year old male patient was admitted to the hospital with temperature of 103°, chills and fever. X-ray studies revealed extensive pneumonia in the right lower lobe of the lung. Blood cultures were positive for *Klebsiella pneumoniae*. Using conventional Wright's stain, before treatment with antibiotics, the white blood cell count was 36,000 per mm$^3$. The blood contained many promyelocytes, myelocytes and metamyelocytes as well as mature neutrophils.

Chromosomal studies diagnosed the patient as having a leukemoid reaction and not leukemia.

A heparinized peripherial blood sample was obtained and subjected to supravital, fixative free analyses by using a five drop fraction of blood with one drop of a freshly prepared 1% aqueous solution of basic orange 21. The dye specimen was agitated and viewed immediately as a wet mount. Promyelocytes were distinguished by primary granules stained a bright orange-red or crimson to magenta. Myelocytes had a smaller proportion of yellow granules to orange-red granules in the cytoplasm as compared to the metamyelocytes, the red granules (lysosomes) of the latter were clustered in the smaller portion end of the cytoplasm imparting a prominent two tone pattern. The neutrophils were identified by a mainly yellow secondary granular cytoplasm. The results demonstrated that basic orange 21 dye provided instantaneous differentiation of the various recognized stages of maturation of granulocytic cells, and that they may be identified in blood or tissue fluid preparations.

DEVELOPMENT OF THE INVENTION

In the foregoing specification and examples there has been some emphasis on the importance of the advances here disclosed in application to automated differential leukocyte computing devices. There is no known "off the shelf" equipment capable presently without some modification of taking advantage of the method herein disclosed which has been employed manually. Those skilled in the art and working in the field of medical technology are aware of the importance of rapid, accurate determination of the various differential leukocyte counts for a variety of ends. It has been estimated that in the United States each day an half million differential leukocyte counts are performed, most of them by manual techniques at an annual cost of over 750 million dollars.

Such counts, whether manual or automated, have a fundamental requirement of identification, spectral differentiation, enumeration and diagnostic aid in practice of medicine. The foregoing advance in these fundamentals will no doubt give rise to advances in ancillary automated equipment as herein indicated.

Blood counts as are of concern herein, whether manual or automated, are vital aids in examination and determination of the nature of disease. Fevers of unexplained origin; whether viral or non-pyrogenic infection, pyogenic involving appendix, gall-bladder, fallopian tubes; prognosis of patients with various diseases in various stages; malignancies including Hodgkins disease; pulmonary disease; surveillance of patient treatment with adrenocortical steroids; various kinds of acute and chronic leukemias; differentiation in diagnosis between aseptic infarction of bone and osteomyelitis; bacterial infections and many other medical questions are aided in diagnosis, prognosis and treatment by accurate leukocyte counting, analysis and cytological study.

As used herein, the term metachromatic has relation to not only to the peculiar and unusual quality of the dyestuffs disclosed but to the quality of the various components, illustratively nucleus and cytoplasm, of each of the individual species of leukocytes which metachromatically co-react with something akin to snyergism to produce the differentiation in spectral response which makes the described advances in cytochemistry possible. In essence, each white blood cell species sorbs (or fails to sorb) a single metachromatic dyestuff in some unusual and unique manner so that each dye-sorbed cell reflects an individual and different light spectra.

It has been well known that certain granular leukocytes have different affinities for various dyes, that is, basophils have affinity for basic dyes, eosinophils have affinity for acid dyes and that neutrophils do not stain intensely with either acid or basic dyes, no morphological features or chemical behavior is suggested that makes possible the specificity of basic orange 21 in making such sharp distinctions as here found between T-lymphocytes and B-lymphocytes and the unusual distinction in bands.

This is the more arcane when it is found that basic orange 22, which varies as to its structural chemistry only in two secondary group position variations as discussed earlier, is totally inoperative for the utilities set out herein.

Identification, differentiation and enumeration of monocytes has valuable diagnostic significance. Increased numbers of monocytes in the blood may indicate the presence of active tuberculosis, septicemia or blood poisoning and lymphomas like Hodgkins disease in diagnosis. Increased number of monocytes in the blood of persons recovering from hypoplastic or aplastic anemia may herald a favorable prognosis for the patient. Rapid and accurate microscopic analyses of monocytes by this method favors extended application of a valuable technique.

Detection, identification and enumeration of polymorphonuclear leukocytes (neutrophils) are critical parameters in all blood evaluations. They are especially vital in the diagnosis of acute infections like pneumonia or peritonitis where the number of neutrophils are increased. They are important in monitoring patients receiving chemotherapy and for radiation therapy. Decreased numbers can occur in overwhelming infection, as a manifestation of drug toxicity, hyperactivity of the spleen and in acute leukemia.

If the absolute neutrophil count falls below 1000 $mm^3$, the risk of infection increases sharply. The specific dye of this invention instantly stains the granules or lysosomes which are characteristic identifying structure of polymorphonuclear leukocytes or neutrophils.

Eosinophils are involved in allergic reactions, as are the basophils. Lymphocytes are involved in inflammation and to a greater extent in immune reactions and response to antigens (foreign bodies). Eosinophils are here instantly identified by the large orange granules in the cytoplasm, and the lobular configuration of the unstained nucleus.

Eosinophil counts are used in following the medical administration of adrenocorticotrophic hormone ACTH in the treatment of clinical conditions. Prior methods introduced confusing artifacts and indefinite forms confusingly similar to the eosinophils. Accuracy of the blood cell count with the prior art decreases with the time between blood sample preparation and completion of the count. Multiple dyes are essentially used. Acid and base staining is often required. The prior art dyes used tend to crystallize out of solution on standing.

Lymphocytes, specifically identifiable as a class with blue borrel, are known to be related to inflammation and immunity. They are increased in number in the blood of persons with chronic lymphatic leukemia and in persons with pertussis (whooping cough). The count may be decreased in patients undergoind chemotherapy and radiotherapy, in patients with lymphoma and various types of hereditary immunological deficiencies.

Basophils have a cytoplasm which contains large granules that are rich in cationic substances like heparin, serotonin and histamine. They are involved, for example, in allergic reactions.

The principal advance in this C.I.P. application has been the discovery that there is presently one unique dye which differentially stains lymphocytes, previously stained only as a class by blue borrel at lower temperatures which can be used in a single pure form for both manual and automatic identification and study of each indicated species. It is clear that there may be found potential advantages in using combinations of the dyes disclosed in the parent application with the specific basic orange 21 of this C.I.P.

In prior art studies of T-cells and B-cells their differentiation has involved more complex biochemical preparations and procedures including: 1. Acid phosphatase (enzymes); 2. Non-specific esterase; 3. Fragments of human immunoglobulins (Ig G); 4. Fluorescent dyes and 5. SRBC - sheep red blood cell preparations having a useful life of about 14 days, it is the basis for rosette formation for identification of T-cells, and is temperature dependant.

T-lymphocytes are found in 60-80% in peripheral blood and 85-90% in the thoracic duct. These cells are known to be related to allograft rejections and both T-cell and B-cells are important considerations in immunology and pathology. B-cells are fewer in number and are from 10-30% in germinal center and medullary cords.

Drug addicts show significant reduction in T-cells.

The vast majority of congenital immunological disorders have relation to T-cell and B-cell systems. Neoplastic diseases are also known to involve the immunogenetic system and patients are recognized to have abnormalities of T-lymphocyte and B-lymphocyte systems. Adult lymphomas are most often of B-cell origin. Childhood lymphomas, on the other hand, bear T-cell markers believed to relate to the more active thymus in early childhood.

Chromic lymphocytic leukemia is a B-cell related, leukemic cells are B-cells and none have T-cell clusters. From this brief sketch, the importance of ready identification, comparison and enumeration of these cells has far reaching significance.

In all instances, microscopic observations are intended to include white light illumination which is standardly used in clinical microscopy. Automated differential leukocyte counting is presently made possible with normal white light illumination, but so far as is known, no present commercial equipment is directly useful here. This invention in method makes feasible and overcomes many of the problems delaying successful development of computer related automatic differential leukocyte counting means.

The term metachromatic believed first used by Ehrlich (1897) describes a stain which changes apparent color when sorbed by certain cells. The dye is said to exhibit metachromasia and has been observed as a property of relatively few pure dyes, chiefly basic cationic dyes including methines, polymethines and carbocyanines which color tissue elements in a different color. Metachromasia is also defined as the assumption of different color spectra by different substances when stained by the same dye. In cytology as here, metachromatic granules or other cell elements are those which assume a color different from that of the dye used to stain them.

Inherent in the above discussion of the terms metachromatic and metachromasia, two factors are involved. One is the biological cell (and its specialized parts), which has been called "metachromatic" or "chromotropic" and is a quality or character of the biological cell specimen, and the other is the quality of the dye. Very few dyes possess whatever quality is essential to stimulate structure(s) within a cell to exhibit metachromasia. Conn (9th Edition) reports "pure dyes showing this reaction are few in number". Few reports found indicate that the phenomena has heretofore involved more than two distinct color spectra. In one instance, "a light green-blue nuclear stain with a violet metachromasia for cartilage" was reported. However, with stains being normally applied to fixed tissues whose chemical and physical nature is altered by the usual prestaining preparatory procedures, essential cooperation between the character of the natural biological structures within a cell specimen (may be thereby altered and rendered not sensitive to what might otherwise react) so that dye sorption does not occur.

Fluorescent dyestuffs are well known. In fluorescence, more light energy is emitted over select narrow frequencies than is absorbed in these select frequencies, although the total light reflected is not more than the total light absorbed. Fluorescent metachromasia is known (example certain dyes in the acridine chromophore class). However, this quality of metachromasia is not within the scope of the term "metachromasia" as used herein. The term here as used is in accord with the use of the term as found in Conn (9th Edition), and Gurr's in "Synthetic Dyes in Biology, Medicine and Chemistry" and Gurr's "Rational Use of Dyes in Biology" where no references to "fluorescent metachromasia" have been noted.

However, useful dyes for the purposes of this invention may exhibit some fluorescence, such as a fluorescent quality in solution, but do not depend upon the quality of "fluorescent metachromasia" to be operative for the purposes of this invention. The term metachromasia as herein used is independent from fluorescent response to any given wave length of light.

Specific chromophoric groups have been used as in the "Colour Index" for further classification of dyes. Dyes found useful for the purposes of this invention embrace only very few dyes in the identified classes. Of greatest interest and of most promise as a class are the methine, polymethine, quinoline and carbocyanine dyes where the so identified chromophoric group bridges between other chromophoric groups in the cationic class. Often, for example, a methine or polymethine group is found to bridge between one or more quinoline bearing chromophores.

Representatives useful have also been found under the broad class identified in the art as aryl methanes; of which broad class one of the few useful selected dyes for the purposes of this invention is a triamino triaryl methane (Hofmans Violet) and another a phenyl naphthyl methane (Night Blue). These are the only two of that generic class found operative out of a very large number in this class tested. Other classes known to have only a few operative species include oxazines, thiazines and indamines. None of the other classes of chromophoric groups listed in the Colour Index Classification system have so far in my research produced operative species.

The broad class of basic dyes which embraces the metachromatic dyes of this invention comprise those in which the auxochrome group is a primary, secondary or tertiary amine group; one nitrogen at least functioning as a quaternary nitrogen atom and upon addition of a colorless anion, most often a halogen acid, can form a salt. As the halogen acids are relatively strong as compared with the ammonium base, they are most often mildly acid in reaction, or exhibit an acid pH. The organic chromophoric group is a cation, carrying a positive charge and the halogen ion provides the anion or negative charge.

Subsequent to the filing of the parent application where basic orange 21, a polymethine dye, was first found to be promising for the purposes of white blood cell classification, samples of other basic orange dyes identified in the Color Index, namely; 22, 27, 42, 44 and 46 were found and checked for metachromasia. These were dyes reported to be in the polymethine class. Basic oranges 24, 25, 26 and 28 were also tested. None of these dyes were polymethines. Of all the basic oranges tested including polymethine and methine basic oranges, only basic orange 21 dye was of utility for the purposes herein.

As basic red 13 and basic violet 16, of the polymethine class had been established as metachromatically valuable for blood cell identification in the parent application, the search was extended to cover similarly identified and available methine and polymethine reds and violets of the Color Index. Basic reds 14, 15, 27, 37, 68 and 102 upon testing were found to lack that quality of metachromasia essential to stain monocytes and/or other leukocytes. However, it was established that basic red 35, 36 and 49 (all polymethines) were useful for differential metachromatic staining of white blood cells as originally of interest in the parent application.

Basic violet (dyes) 7, 1 5, 16, 39 and 40 (again all polymethines) were found useful and operative. However, basic violet 14, not classed as a polymethine in the Color Index, did not develop metachromasia in dyeing white blood cells as did basic violet 16.

While it is submitted that the Color Index identifies all of the above dyes, spectral curves will be depended upon as the final arbiter for all dye identifications herein as these curves related to the foregoing Color Index numbers are made available.

Having described the best mode presently known to practice the disclosed invention, what is claimed is:

1. A method for analysis of human blood whereby normal or pathological blood leukocytes including leukemic lymphoblasts present in a human blood specimen are made selectively spectrally determinant which comprises preparing at least one leukocyte containing specimen in a supravital, fixative-free state by contact in an aqueous environment with the dye basic orange #21; each of the above dye-stained species present in said classes of blood components sorbing said dye metachromatically and differentially as exhibited by (1) the presence or absence of characteristic color and pattern of the nucleus and cytoplasm and (2) the relative number, size, arrangement or pattern and color or colors of the granules present, or not present in the cytoplasm.

2. The method of diagnostic aid in patient examination and disease treatment which comprises subjecting leukocytes of a patient donor blood specimen in a fixative-free state to supravital staining in an aqueous environment with the dye basic orange #21; microscopically comparing the donor leukocytes stained or nonstained thereby with a known non-diseased blood specimen similarly prepared being the base standard for comparison, noting differences from said standard in the tinctorial properties of the granules in the cytoplasm and nucleus present in said donor sample being diagnosed, thereby determining the presence or absence of disease affecting one or more of the leukocytes disclosing material modification from said standard in said donor specimen fraction.

3. A method of normal and pathologic human blood analysis whereby lymphocytes or leukemic lymphoblasts present in human blood specimen are made selectively spectrally determinant which comprises treating at least one supravital human blood specimen fraction in a fixative-free state by contact in an aqueous environment with at least one basic quaternary cationic dyestuff having the essential chromophoric combination of structure and groups present found in basic orange #21 thereby metachromatically differentiating the individual species of said cells from one another enabling classification and enumeration of identified species present in said analysis.

4. A white light absorbance method of human blood analysis whereby optical differentiation, enumeration and comparison of each of the individuals in a granulocytic myeloid series including, when present; promyelocytes, myelocytes, metamyelocytes, bands and neutrophils is achieved by metachromatically staining at least one supravital, fixative-free human blood specimen fraction by contact in an aqueous environment with basic orange #21 dye; thereby differentiating the promyelocytes by the presence of predominantly orange-red primary granules in the cytoplasm; myelocytes by a mixture of predominantly orange-red primary granules in a smaller crescent and a lesser mass of yellow secondary granules in a thicker crescent of the cytoplasm; metamyelocytes by a smaller mass of orange-red primary granules in the smaller crescent and yellow secondary granules in larger proportionately thicker mass of a second portion of the crescent constituting the cytoplasm; the bands by a relatively small cluster of primary orange-red granules in a dominant field of secondary yellow granules constituting the cytoplasm and the neutrophils by substantially all the granules of the cytoplasm being yellow; each member of the foregoing series having an apparently decreasing proportionate area (volume) of the nucleus remaining substantially unstained, the first three members of the series of generally larger overall (area or volume) cell size than the last two members of the series.

5. In a dye staining method for differential analysis of human blood specimen whereby mature leukocytes, immature leukocytes and other blood fragment components present in said specimen are made selectively determinant, one from the other, enabling differentiation and enumeration of all of said blood component species consisting essentially of neutrophils, eosinophils, basophils, lymphocytes, lymphoblasts and monocytes as well as myeloblasts, promyelocytes, myelocytes, metamyelocytes, platelets, bands, T-cells and B-cells; the method which comprises metachromatically staining a human blood containing specimen within a temperature range of 21°-40° C. in an aqueous, supravital, fixative-free state with substantially chemically pure, organic basic quaternary cationic dyestuff comprising basic orange #21; thereafter and thereby enabling identification, differentiation and enumeration of any one or all of the aforesaid blood component species present in said blood specimen under white light absorbance means.

6. The method of claim 5 which further comprises the study and diagnosis of human disease by comparing the stained human blood specimen with a disease-free standard specimen by the steps of evaluating the relative number, size, arrangement or pattern and color or colors or variations in or proportion of colors of the differentially stained human blood cell component species present and pertinent to said study and by the presence, absence or variations in color and pattern of the cell nucleus and by the relative number, size, arrangement or pattern and color or colors or variations in the proportion of colors of the granules in the cytoplasm or absence or presence of color therein as compared with the disease-free standard.

7. The method of claim 5, where the human blood cells in a donor specimen include one or more of the following species; myeloblasts, promyelocytes, myelocytes, metamyelocytes, bands, lymphocytes, B-cells, T-cells or monocytes and each one is thereby made optically identifiable one from the other.

8. The method of claim 5, where the normal or pathologic leukocytes are lymphocytes, B-cells or T-cells, and are each individually indentifiable and capable of identification and enumeration as a part of the said analysis.

9. The method of claim 5 wherein the metachromatically differentiated lymphocytes and lymphoblasts are further identified and enumerated by human observations.

10. The method of claim 5, wherein the metachromatically differentiated lymphocytes and lymphoblasts are further identified and enumerated by physical white light spectra responsive means.

11. The method of claim 5 for analysis of human blood whereby optical identification, differentiation, and enumeration of T-lymphocytes and B-lymphocytes present is achieved by differentiating T-cells present from the B-cells by a cluster of red granules noted in the otherwise unstained cytoplasm of the T-cells, and absence of said cluster of red granules in the instance of the cytoplasm of the B-cells present, the nucleus of said T-cells and B-cells exhibiting a yellow staining.

12. The method of human blood analysis of claim 5 whereby optical differentiation, enumeration and comparison are made possible of bands present therein thereby differentiating band cells from other leukocytes present in said specimen by a relatively small cluster of orange red granules set apart in a cytoplasmic field consisting of a large number of yellow granules about a non-stained nucleus.

* * * * *